US009295843B2

(12) United States Patent
Enrooth et al.

(10) Patent No.: US 9,295,843 B2
(45) Date of Patent: Mar. 29, 2016

(54) AUTOMATIC PACING CONFIGURATION SWITCHER

(71) Applicant: Cardiac Pacemakers, Inc., St. Paul, MN (US)

(72) Inventors: Eric K. Enrooth, Lino Lakes, MN (US); Sunipa Saha, Shoreview, MN (US); Krzysztof Z. Siejko, Maple Grove, MN (US); Kenneth N. Hayes, Blaine, MN (US); Aaron R. McCabe, Edina, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 95 days.

(21) Appl. No.: 13/887,818

(22) Filed: May 6, 2013

(65) Prior Publication Data

US 2013/0310891 A1 Nov. 21, 2013

Related U.S. Application Data

(60) Provisional application No. 61/649,218, filed on May 18, 2012.

(51) Int. Cl.
*A61N 1/362* (2006.01)
*A61N 1/368* (2006.01)
(Continued)

(52) U.S. Cl.
CPC .............. *A61N 1/362* (2013.01); *A61N 1/3686* (2013.01); *A61N 1/36071* (2013.01); *A61N 1/36185* (2013.01); *A61N 1/36507* (2013.01); *A61N 1/36535* (2013.01); *A61N 1/36585* (2013.01)

(58) Field of Classification Search
CPC . A61N 1/36132; A61N 1/362; A61N 1/3686; A61N 1/36535; A61N 1/36585; A61N 1/37; A61N 1/3706
See application file for complete search history.

(56) References Cited

U.S. PATENT DOCUMENTS

| 6,247,474 | B1 | 6/2001 | Greeninger et al. |
| 6,704,598 | B2 | 3/2004 | Ding et al. |
| 7,092,761 | B1 | 8/2006 | Cappa et al. |

(Continued)

FOREIGN PATENT DOCUMENTS

WO   WO-2013173102 A1   11/2013

OTHER PUBLICATIONS

"Wong-Baker Faces Pain Rating Scale," accessed Mar. 14, 2015, wikipedia.com, http://en.wikipedia.org/wiki/Wong-Baker_Faces_Pain_Rating_Scale.*

(Continued)

*Primary Examiner* — Michael Kahelin
(74) *Attorney, Agent, or Firm* — Schwegman Lundberg & Woessner, P.A.

(57) ABSTRACT

A system or apparatus can provide electrostimulations via an electrode configuration that can be selected from multiple electrode configurations, the electrostimulations of the type for inducing a desired heart contraction, or a neurostimulation response. The system or apparatus can allow communicating with an external device to receive an input indicating a degree of patient discomfort with an electrostimulation delivered using a first electrode configuration, and can associate information about the degree of discomfort with information about the corresponding first electrode configuration for use by a controller circuit in determining a second electrode configuration for delivering a subsequent electrostimulation.

16 Claims, 7 Drawing Sheets

(51) Int. Cl.
  *A61N 1/36* (2006.01)
  *A61N 1/365* (2006.01)

(56) References Cited

U.S. PATENT DOCUMENTS

| | | |
|---|---|---|
| 7,215,997 B2 | 5/2007 | Yu et al. |
| 7,330,760 B2 | 2/2008 | Heruth et al. |
| 7,395,113 B2 | 7/2008 | Heruth et al. |
| 7,447,545 B2 | 11/2008 | Heruth et al. |
| 7,463,927 B1 | 12/2008 | Chaouat |
| 7,491,181 B2 | 2/2009 | Heruth et al. |
| 7,558,627 B1 | 7/2009 | Turcott |
| 7,792,583 B2 | 9/2010 | Miesel et al. |
| 7,805,196 B2 | 9/2010 | Miesel et al. |
| 7,840,265 B2 | 11/2010 | Perschbacher et al. |
| 7,908,013 B2 | 3/2011 | Miesel et al. |
| 7,957,797 B2 | 6/2011 | Bourget et al. |
| 7,957,809 B2 | 6/2011 | Bourget et al. |
| 8,135,473 B2 | 3/2012 | Miesel et al. |
| 8,150,531 B2 | 4/2012 | Skelton |
| 8,190,253 B2 | 5/2012 | Heruth et al. |
| 8,200,340 B2 | 6/2012 | Skelton et al. |
| 8,209,028 B2 | 6/2012 | Skelton et al. |
| 8,219,206 B2 | 7/2012 | Skelton et al. |
| 8,231,555 B2 | 7/2012 | Skelton et al. |
| 8,231,556 B2 | 7/2012 | Skelton et al. |
| 8,280,517 B2 | 10/2012 | Skelton et al. |
| 8,290,596 B2 | 10/2012 | Wei et al. |
| 8,315,710 B2 | 11/2012 | Skelton et al. |
| 8,323,218 B2 | 12/2012 | Davis et al. |
| 8,332,041 B2 | 12/2012 | Skelton et al. |
| 8,388,555 B2 | 3/2013 | Panken et al. |
| 8,396,554 B2 | 3/2013 | Miesel et al. |
| 8,396,565 B2 | 3/2013 | Singhal et al. |
| 2003/0032992 A1 | 2/2003 | Thacker et al. |
| 2006/0229687 A1 | 10/2006 | Goetz et al. |
| 2006/0241722 A1 | 10/2006 | Thacker et al. |
| 2006/0259097 A1 | 11/2006 | Hickman et al. |
| 2008/0234780 A1* | 9/2008 | Smith et al. ............. 607/45 |
| 2008/0294215 A1 | 11/2008 | Sathaye |
| 2009/0043351 A1 | 2/2009 | Sathaye et al. |
| 2009/0043352 A1 | 2/2009 | Brooke et al. |
| 2009/0054947 A1 | 2/2009 | Bourn et al. |
| 2009/0210024 A1 | 8/2009 | M. |
| 2010/0174338 A1 | 7/2010 | Gilkerson et al. |
| 2010/0185268 A1 | 7/2010 | Fowler et al. |
| 2010/0280440 A1* | 11/2010 | Skelton et al. ............ 604/66 |
| 2010/0305638 A1 | 12/2010 | McCabe et al. |

OTHER PUBLICATIONS

"Medtronic EnPulse™ Pacemaker Programming Guide", (2003), 340 pgs.

Hamann, Jason J., et al., "Systems for Patient Control of Implantable Medical Device Therapy", U.S. Appl. No. 61/333,589, filed May 11, 2010.

"International Application Serial No. PCT/US2013/039699, International Preliminary Report on Patentability mailed Nov. 27, 2014", 12 pgs.

"International Application Serial No. PCT/US2013/039699, International Search Report mailed Jul. 26, 2013", 5 pgs.

"International Application Serial No. PCT/US2013/039699, Written Opinion mailed Jul. 26, 2013", 10 pgs.

* cited by examiner

AUTOMATIC PACING CONFIGURATION SWITCHER

CLAIM OR PRIORITY

This application claims the benefit of priority under 35 U.S.C. §119(e) of U.S. Provisional Patent Application Ser. No. 61/649,218, filed on May 18, 2012, which is herein incorporated by reference in its entirety.

BACKGROUND

When functioning normally, the heart produces rhythmic contractions and is capable of pumping blood throughout the body. The heart has specialized electrical conduction pathways in both the atria and the ventricles that normally enable excitation impulses initiated from the sino-atrial (SA) node to be rapidly conducted throughout the myocardium. These specialized conduction pathways normally conduct depolarizations from the SA node to the atrial myocardium, to the atrio-ventricular node, and to the ventricular myocardium to produce a coordinated contraction of both atria and of both ventricles.

Cardiac rhythm management (CRM) devices have been developed that can provide electrostimulations to one or more heart chambers in an attempt to improve the rhythm or coordination of atrial or ventricular contractions. CRM devices can include circuitry to sense one or more signals from the heart. CRM devices can include an electrostimulation circuit for providing electrical stimulation to the heart. One or more leads can extend from the CRM device into a patient's heart chamber or into one or more veins of the heart. The lead can include one or more electrodes. The electrodes can be used to sense an electrical signal or to deliver electrical stimulation to the heart. This can include using one or more electrostimulation configurations for treating cardiac arrhythmias or dyssynchrony.

Sathaye et al. U.S Patent Application Publication No. US 2009/0043351 discusses a method and apparatus to perform electrode combination selection.

Ding et al. U.S. Pat. No. 6,704,598 discusses a cardiac rhythm management system selecting between multiple same-chamber electrodes for delivering cardiac therapy.

OVERVIEW

Some patients may feel discomfort with an existing electrostimulation configuration. This discomfort can occur because of unwanted, or not medically necessary, phrenic nerve stimulation or muscle stimulation in the vicinity of the implanted device (e.g. "pocket stimulation"). Stimulating the phrenic nerve can cause a contraction of the diaphragm, which can cause a hiccup reflex. Patients who experience phrenic nerve stimulation or muscle stimulation may schedule a follow-up visit with a healthcare provider. During the visit, alternate electrostimulation configurations or parameters (e.g., different electrode configurations, different electrostimulation energy delivery parameters, or combinations thereof) can be tested or chronically programmed, such as to reduce the discomfort. Consequently, the CRM devices can be reprogrammed by a healthcare provider to provide the alternative electrostimulation configuration or parameters for delivering the electrostimulation. The process can be tedious, time consuming, and expensive, which can ultimately increase the burden on a hospital or its staff.

This document discloses examples of a cardiac rhythm management system and related methods that can adjust the electrostimulation configuration or one or more parameters, or both, to reduce patient discomfort caused by, for example, phrenic nerve stimulation or unintended muscle stimulation. The system can switch from a first electrode configuration to a second electrode configuration, or can adjust one or more electrostimulation parameters based on an input indicating a quantified degree of patient discomfort with the then-current electrostimulation configuration or parameters. Examples of methods, apparatuses, and systems are discussed herein.

Among other things, the present inventors have recognized a need for an apparatus and a method that can allow a health care provider or a patient to interact with a CRM or other medical device, such as to test one or more electrostimulation configurations or parameters, or to switch to an alternate electrostimulation configuration or parameter. This can help reduce patient discomfort in a timely manner without requiring any interventional interaction from the health care provider or the patient.

A cardiac rhythm management system, method, and apparatus are described herein. The apparatus can include an implantable electronics unit. The implantable electronics unit can include an electrostimulation circuit that can be configured to provide electrostimulations using a first set of electrostimulation parameters via a first electrode configuration that can be selected from multiple electrode configurations. A communication circuit can be configured to communicate with an external device, such as to receive an input indicating a degree of patient discomfort with the electrostimulation delivered using the first electrode configuration. A controller circuit can be coupled to the electrostimulation circuit and the communication circuit. The controller circuit can be configured to a second set of electrostimulation parameters or a second electrode configuration based on the degree of patient discomfort.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE FIGURES

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, various examples discussed in the present document.

DETAILED DESCRIPTION

Figure 1:
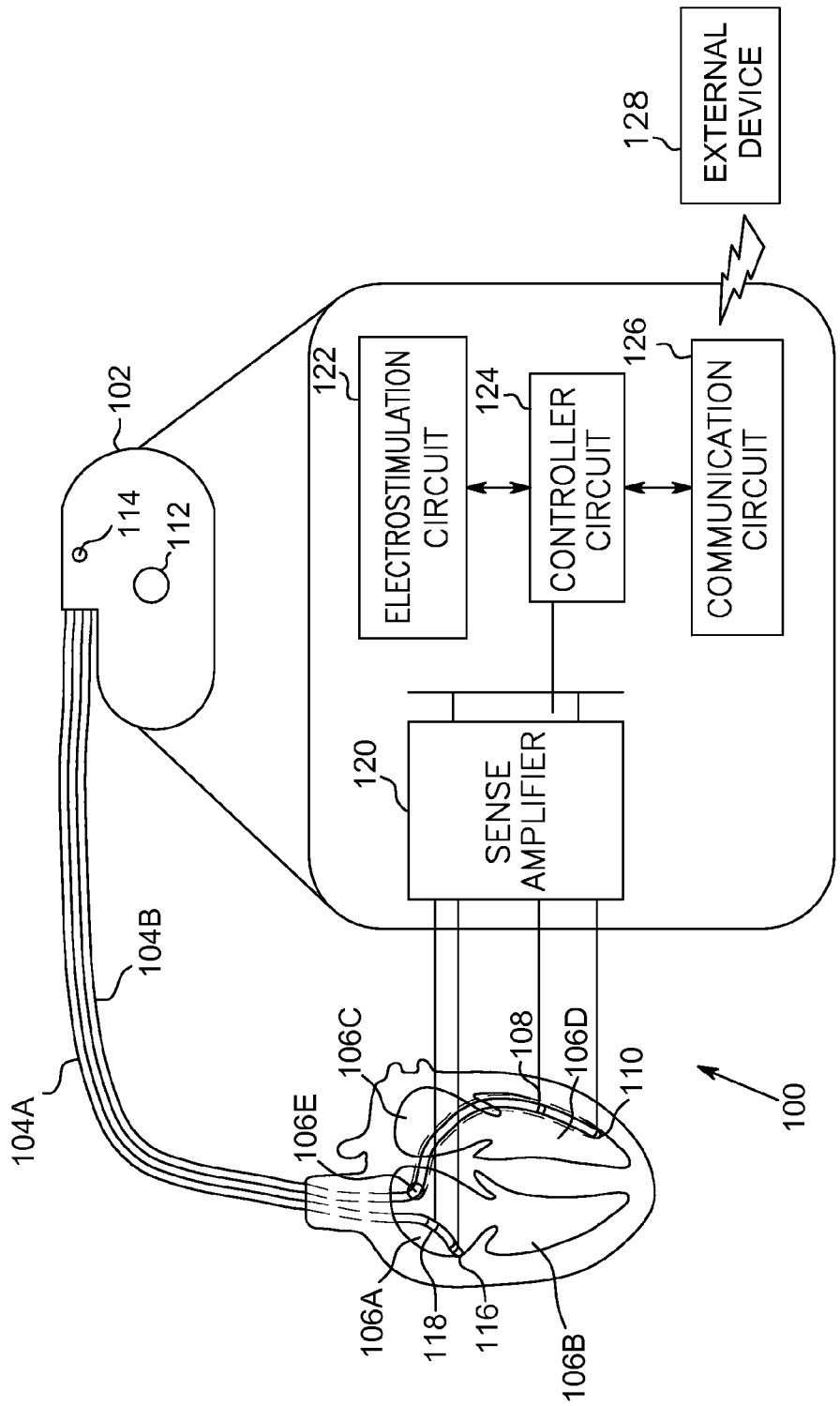
FIG. 1 is a schematic diagram illustrating generally, among other things, an example of portions of a cardiac rhythm management apparatus or system and an environment in which it can be used.

FIG. 1 is a diagram illustrating generally an example of portions of a cardiac rhythm management (CRM) system that can include a CRM apparatus 100, which can be coupled to a heart 106, and an environment in which it can be used. The apparatus 100 can include an implantable electronics unit 102. The implantable electronics unit 102 can be coupled by leads 104 A-B to the heart 106. The heart 106 includes four chambers: a right atrium 106A, a right ventricle 106B, a left atrium 106C, and a left ventricle 106D. The heart 106 also includes a coronary sinus 106E, which is a vessel that extends within the tissue of the heart wall from the right atrium 106A toward the left ventricular free wall. The coronary sinus 106E is considered to include the great cardiac vein or tributary vessels.

The lead 104A can include one or more electrodes (e.g., electrical contacts) such as electrodes 116 and 118. The electrode can be sized, shaped, or otherwise configured to be associated with, or around, or near, the right atrium 106A of the heart 106. For example, the one or more electrodes can include a tip electrode 116 or a ring electrode 118. The one or more electrodes can be used for sensing one or more signals (e.g., one or more cardiac signals) or for delivering pacing or other electrostimulation therapy to the heart. The one or more electrodes can be considered to be "associated" with a particular heart chamber by inserting the electrode into that heart chamber, by inserting the electrode into a portion of the heart's vasculature near that heart chamber, by epicardially placing the electrode outside that heart chamber, or by any other technique of configuring and situating an electrode for sensing one or more signals or providing electrical energy with respect to that heart chamber. The lead 104B can be introduced into the coronary sinus 106E or the great cardiac vein or one of its tributaries. The lead 104B can include one or more (e.g., two, three, four, or other number) electrodes, such as electrodes 108 and 110, that can be sized, shaped, or otherwise configured to be associated with the left ventricle 106D. The implantable electronics unit 102 can include one or more other electrodes, such as a housing electrode 112 or a header electrode 114. The one or more electrodes on the implantable electronics unit 102 can be used for unipolar sensing or electrostimulation in conjunction with a lead electrode, such as electrodes 108, 110, 116, and 118. Bipolar or multipolar sensing or electrostimulation can be implemented using two or more lead electrodes. For example, bipolar sensing or electrostimulation can be provided between the electrode 116 and the electrode) 18, between the electrode 108 and the electrode) 10, between the electrode 116 and the electrode 108, between the electrode 116 and the electrode 110, between the electrode 118 and the electrode 108, between the electrode 118 and the electrode 100, or between any other lead electrodes. For instance, an RV lead can be provided. The RV lead can include one or more of tip, ring, coil or other electrodes that can be used for bipolar pacing, extended bipolar pacing (e.g., with an intracardiac electrode located on another lead), or unipolar pacing.

The implantable electronics unit 102 can include a sense amplifier 120. The sense amplifier 120 can be coupled to one or more electrodes (e.g., 108, 110, 116, or 118) such as for sensing an electrical depolarization corresponding to a heart chamber contraction. The one or more electrodes (e.g., 108, 110, 116, or 118) can be used to sense or deliver pace electrostimulations to one or more chambers of the heart 106, such as the left ventricle 106D, the right ventricle 106B, the left atrium 106C, or the right atrium 106A. An electrostimulation circuit 122 of the apparatus 100 can be configured to generate and deliver one or more controlled electrical stimulation pulses such as via two or more electrodes, which can include one or more of the electrodes 108, 110, 116, 118, or one or more other electrodes as provided. The electrical stimulation pulses can be used to induce the heart 106 to beat, such as at a hemodynamically sufficient rate, to improve or coordinate the spatial or spatiotemporal activation pattern of one or more heart beats (e.g., cardiac resynchronization), to increase the strength of one or more of the heart beats, or for one or more other purposes, such as to support one or more cardiac functions, such as per a specified therapy.

The implantable electronics unit 102 can include the electrostimulation circuit 122, a controller circuit 124, or a communication circuit 126. The electrostimulation circuit 122 can be configured to provide one or more electrostimulations, such as to pace the heart. The electrostimulation pulses can be delivered via an electrode configuration, which can be selected from multiple available electrode configurations (e.g., which can include one or more unipolar configurations or one or more bipolar configurations, or both). A particular combination of the electrodes (108, 110, 112, 114, 116, 118) can represent an electrode configuration. The electrostimulations can be of the type for inducing a heart contraction or for inducing a neurostimulation response. The electrostimulations can be delivered by the electrostimulation circuit 122, such as through one or more leads or through one or more electrodes.

The communication circuit 126 can be configured to communicate with a local or remote external device 128, such as to receive an input from a patient or a physician. The patient or physician input can include information indicating a degree of patient discomfort with an electrostimulation delivered using a first electrode configuration. Examples of conditions that may cause patient discomfort can include phrenic nerve stimulation or other extracardiac stimulation, such as muscle stimulation or pocket stimulation at the site of implantation. The external device 128 can communicate with the implantable electronics unit 102 to switch from a first electrode configuration to a second electrode configuration (which can be selected from multiple available electrode configurations) or to adjust one or more electrostimulation parameters (e.g., amplitude, pulsewidth, etc.) The patient or physician input can provide information that can be indicative of a degree of patient discomfort, which, in turn, can depend on the particular patient's tolerance toward pain or other discomfort. In other words, the degree of patient discomfort may be patient specific.

The controller circuit 124 can be coupled to the electrostimulation circuit 122 and the communication circuit 126. The controller circuit 124 can be configured to associate or store the input information about the degree of patient discomfort with a corresponding electrostimulation electrode configuration or one or more other electrostimulation parameters. The patient or physician input information can be used in selecting a second electrode configuration from multiple available electrode configurations or for adjusting one or more of the electrostimulation parameters. The second electrode configuration or the adjusted one or more electrostimulation parameters can then be used for delivering the electrostimulation. The controller circuit 124 can be operable on programmed instructions. The instructions can associate information about the degree of patient discomfort with electrostimulation information about the corresponding first electrode configuration, such as for use in selecting the second electrode configuration from the multiple available electrode configurations.

The controller circuit 124 can be configured to report information about the electrostimulation configuration, the degree of patient discomfort, or other information, such as to the external device 128. In an example, the controller circuit 124 can report physiological information or device information, such as battery capacity, lead impedance, or other device information about the implantable electronics unit 102 or associated leads to the external device 128.

Figure 2:
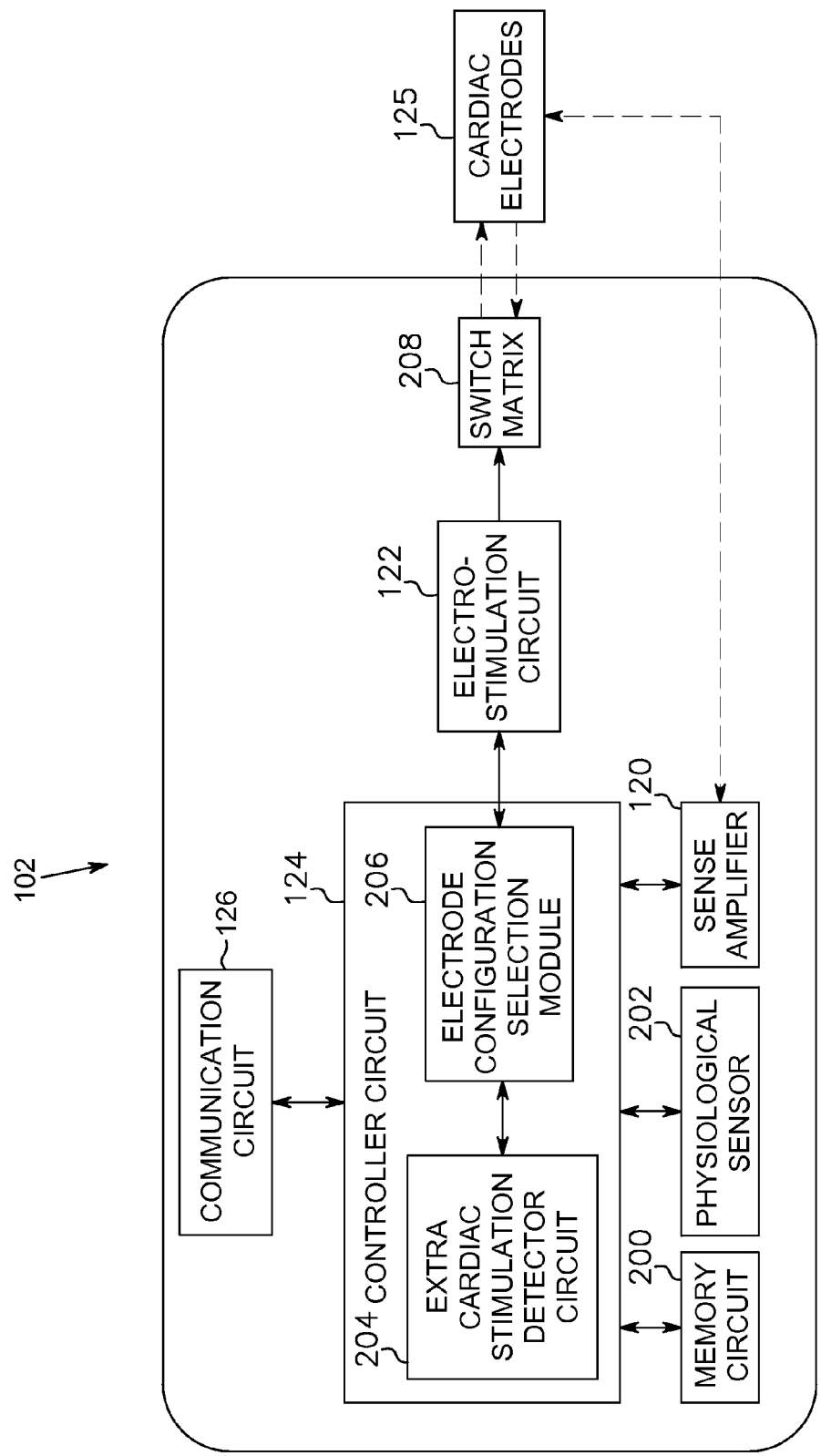
FIG. 2 is an example of a detailed block diagram of the implantable electronics unit of FIG. 1.

FIG. 2 is a block diagram of an example of the implantable electronics unit 102, which can be coupled to one or more electrodes (e.g., 108, 110, 112, 114, 116, 118). The controller circuit 124 can include or can be coupled to a memory circuit 200. The controller circuit 124 can be configured, such as by one or more instructions that can be stored in the memory circuit 200, to monitor physiological information or to deliver electrical stimulation or other therapy. The electrical stimulation therapy can be delivered using a particular electrode configuration that has been selected from multiple available electrode configurations using information about the degree of patient discomfort. A list of the multiple available electrode configurations, and corresponding information, such as the electrostimulation parameters being used therewith, or the degree of patient discomfort associated therewith, can be stored in the memory circuit 200. The memory circuit 200 can be used for storing program instructions or data, which can be accessed by the controller circuit 124. The memory circuit 200 can also be used to store information identifying or about the first electrode configuration or the second electrode configuration or other electrode configurations.

The memory circuit 200 can be configured to store the input information about the degree of patient discomfort associated with one or more individual electrode configurations of the multiple available electrode configurations. Such discomfort information can be stored in association with an indication of the corresponding electrode configuration associated with other specific configuration parameters, what were used for such degree of patient discomfort. Other information associated with a particular electrode configuration can be stored in the memory circuit 200 in association with an indication of the corresponding particular electrode configuration. Such stored electrode configuration information can include one or more of an associated activation threshold, an electrostimulation energy (e.g., amplitude, pulse width, etc.), or one or more other electrostimulation parameters, one or more measured values (e.g., electrode impedance, physiological information, etc.), program instructions, or other information. For example, the memory circuit 200 can be configured to store information about the electrostimulation energy in association with an indication of the corresponding particular electrode configuration of the multiple available electrode configurations, and also in association with the corresponding input information about the degree of discomfort associated with that particular electrostimulation energy and that particular electrode configuration. Based on this information, previously-obtained data of the patient can be used to identify the one or more electrode configurations in association with the corresponding electrostimulation energy levels. This information can be used to automatically identify, recognize, or select one or more particular electrostimulation configurations (e.g., electrode configuration together with electrostimulation energy configuration) by which the patient discomfort could be reduced. Also, the association of this information with the patient discomfort information can make it possible to decide whether a particular electrode configuration can be suitable at particular electrostimulation energy to reduce, mitigate, or avoid current or future patient discomfort by identifying the patient's past experiences.

The controller circuit 124 can be coupled to a physiological sensor 202, such as for sensing posture or other physiologic information of the patient. Various types of sensors can be used for the physiologic sensor 202. Examples can include an accelerometer, an acoustic sensor, an electrical signal sensor, a pressure sensor, a posture sensor, or other sensor. The physiologic sensor 202 can be adapted to sense a physiological parameter, such as patient posture information, which can be sent to the controller circuit 124 so that the controller circuit 124 can automatically adjust the electrical stimulation based on the sensed physiological information such as the patient posture information. The controller circuit 124 can be configured to receive one or more signals pertaining to the patient posture information and information about the corresponding first electrode configuration, which can be used for selecting the second electrode configuration (or the electrostimulation energy to be associated therewith) for delivering a later electrostimulation.

The patient discomfort can depend on an electrostimulation energy associated with a specific electrode configuration. Therefore, it can be advantageous to associate information about the electrostimulation energy with information about a corresponding electrostimulation electrode configuration. For this purpose, the controller circuit 124 can be configured to associate information about electrostimulation energy with information about the corresponding first electrode configuration, such as for use in determining the second electrode configuration for delivering the later electrostimulations. The electrostimulation energy associated with the first electrode configuration can be changed when the electrode configuration is switched to the second electrode configuration, with the objective of maintaining the desired heart contraction or neurostimulation response. In an example, it is determined whether the electrostimulation energy can be safely reduced, using the first electrode configuration, to avoid discomfort while maintaining the desired heart contraction or the neurostimulation response before switching from the first electrode configuration to the second electrode configuration to reduce or avoid the degree of discomfort.

In an example, the controller circuit 124 of the implantable electronics unit 102 can include or be coupled to an extracardiac stimulation detector circuit 204 and an electrode configuration selection module 206. The extracardiac stimulation detector circuit 204 can be configured to determine the presence of phrenic nerve stimulation or other extracardiac stimulations such as muscle stimulation in the vicinity of the implanted device. The controller circuit 124 can be configured to determine the second electrode configuration at least in part by using the information from the extracardiac stimulation detector circuit 204 and information from the input, indicating a degree of patient discomfort with an electrostimulation delivered using the first electrode configuration.

The electrode configuration selection module 206 of the controller circuit 124 can be configured to determine the second electrode configuration using information from the extracardiac stimulation detector circuit 204, but subject to the input indicating the degree of patient discomfort with an electrostimulation delivered using the first electrode configuration and can use information such as a capture threshold, an electrostimulation impedance, or a posture indication, or other information. The controller circuit 124 can be configured to reprogram the electrostimulation circuit 122, such as to switch from delivering electrostimulations using the first electrode configuration to delivering the electrostimulations using a determined second electrode configuration. Such switching can be performed using a switch matrix 208. The electrostimulations can be delivered, such as via the electrodes 210, by the electrostimulation circuit 122. In an example, the controller circuit 124 can first test whether the electrostimulation energy can be adjusted to reduce the degree of the patient discomfort while obtaining a desired heart contraction or neurostimulation response, before switching from the first electrode configuration to the second electrode configuration. For example, the electrostimulation energy can be adjusted to an energy level that is greater than needed for cardiac capture, but that is lower than the phrenic capture threshold. If the desired response cannot be obtained using the first electrode configuration and the adjusted electrostimulation energy, the controller circuit 124 can then switch from the first electrode configuration to a selected second electrode configuration. The selected second electrode configuration can be determined using information from the extracardiac stimulation detector circuit 204 or the information from the input indicating the degree of patient discomfort with an electrostimulation delivered using the first electrode configuration. An example of this method of switching will be described further below.

The switching from the first electrode configuration to the second electrode configuration can be initiated in response to an input received from the local or remote external device 128. The electrostimulation energy can be changed or the electrode configuration can be set automatically by the controller circuit 124, and can optionally be confirmed with the patient or physician such as through a confirmatory input communicated to the implantable electronics unit 102. This input can indicate or confirm whether there is no (or substantially no) discomfort associated with the changed electrostimulation energy using the second electrode configuration (which can be the same electrode configuration or a different electrode configuration than the first electrode configuration). In an example, the input can indicate or confirm whether there is no (or substantially no) discomfort associated with the changed electrostimulation energy using the second electrode configuration in one or more particular postures of the patient, which the patient can be instructed to assume while the changed electrostimulation energy is being tested in that particular posture. Upon receiving a satisfactory confirmation from the patient or physician during such a test mode, the electrostimulation energy associated with the first electrode configuration can be more chronically changed or the first electrode configuration can be more chronically switched to the second electrode configuration, or both.

The input indicative of the patient discomfort can depend on the patient's pain or discomfort tolerance level. For example, a patient A's discomfort may be within that patient's tolerance level. Thus, patient A may not want to switch to the second electrode configuration. By contrast, the tolerance level may be lower in patient B as compared to patient A. Thus, patient B may want to switch to the second electrode configuration. Therefore, the apparatus 100 can use information that can account for the patient's tolerance level (such as the input indicating the patient's degree of discomfort) to determine or select the second electrode configuration, which can optionally be subject to confirmation by the patient or physician. The controller circuit 124 can be configured to trigger automatic reversion from the second electrode configuration to the first electrode configuration, if the input confirming suitability of the second electrode configuration is not received within a specified time period, such as thirty seconds, one minute, two minutes, or any other specified time period, which can be programmable within the controller circuit 124 of the implantable electronics unit 102. In an example, the physician or patient can check the comfort or degree of discomfort associated with the second electrode configuration by changing the one or more postures of the patient. The physician or patient can then provide an input within the specified time period. The input can indicate whether, in such postures, there is no (or substantially no) discomfort associated with the changed electrostimulation energy or the selected second electrode configuration.

In example (1), the controller circuit 124 can be configured to determine the second electrode configuration using information from the extracardiac stimulation detector circuit 204. For example, the implantable electronics unit 102 can change the electrostimulation energy associated with the first electrode configuration or can automatically switch to the second electrode configuration in response to detecting extracardiac stimulation, or patient discomfort.

In example (2), the controller circuit 124 can be configured to determine the second electrode configuration using information from the input indicating the degree of patient discomfort with an electrostimulation delivered using the first electrode configuration. For example, a switch to the second electrode configuration can depend at least in part on the input indicative of discomfort, which, in turn, can depend on the patient tolerance level.

In an example, the controller circuit 124 can be configured to switch between the examples (1) and (2), such as in response to the input indicative of discomfort. Therefore, the implantable electronics unit 102 can operate in either modes represented by the examples (1) or (2), or can combine one or more aspects of the examples (1) and (2) for use together.

Figure 3:
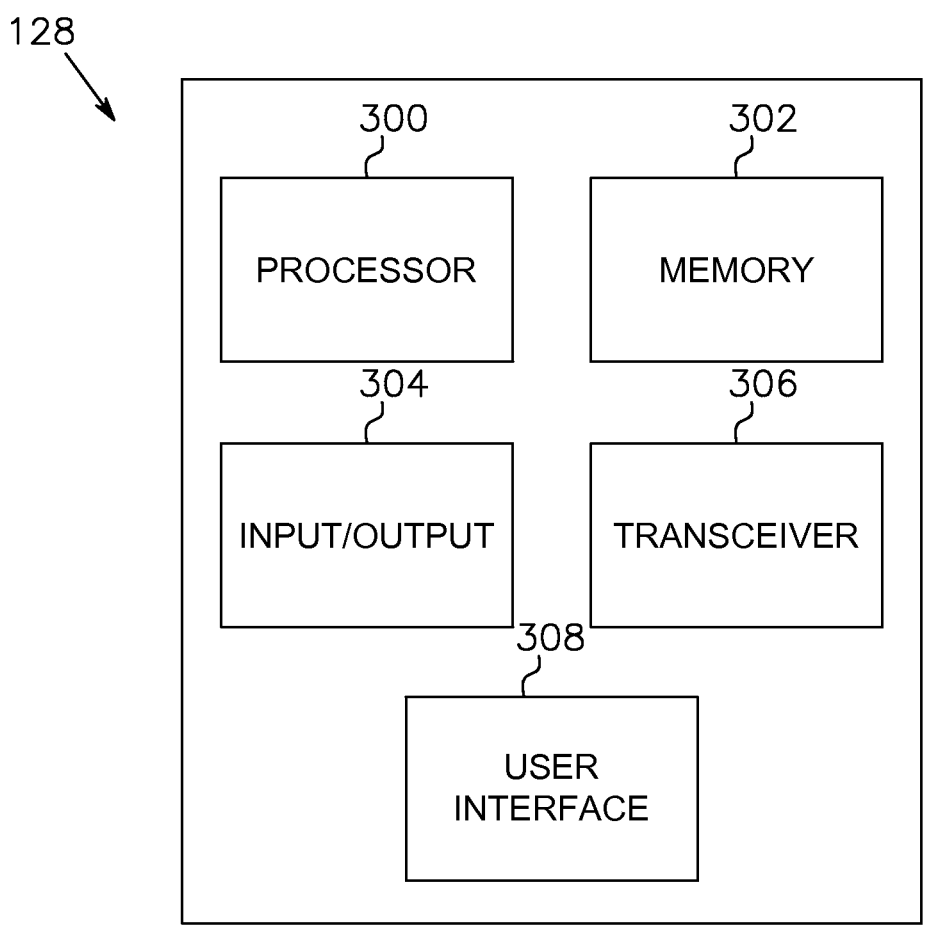
FIG. 3 illustrates an example of a block diagram of an external device (as illustrated in the system of FIG. 1).

FIG. 3 illustrates a block diagram depicting an example of an external device 128 to communicate with the implantable electronics unit 102. Examples of the external device 128 can include, but are not limited to, a personal digital assistant (PDA), a personal laptop, a desktop computer, a handheld device such as a mobile telephone, a tablet computer, or a remote device, or other device. The external device 128 can present various menus on the display screen for controlling operations of the implantable electronics unit 102, or can transfer control of the implantable electronics unit to a local or remote user via a communication link. The external device 128 can serve as a communicator capable of sending information to or from remote devices. The external device 128 can include a processor circuit 300, a memory circuit 302, an input or output (I/O) unit 304, a transceiver 306, a user interface 308, or other components. The processor 300 can include a microprocessor or microcontroller or other circuit that can be capable of being implemented using hardware, software, or a combination of hardware and software. For example, the processor 300 can include a controller circuit to execute one or more instructions stored in the memory circuit 302. The instructions can allow the external device 128 to perform any number of functions. Examples can include communicating data indicating the degree of patient discomfort, programming instructions for providing electrostimulations based on the degree of patient discomfort, or detecting the initiation of a programming session with the implantable electronics unit 102, or any other function. The external device 128 can include a transceiver 306 and associated circuitry, such as a telemetry coil or antenna, to wirelessly communicate with the implantable electronics unit 102. Radio frequency telemetry, inductive telemetry, or another type of wireless communication can be used such as to transmit or receive one or more signals from or to one or more local or remote external devices.

The external device 128 can include one or more input or output (I/O) units 304 such as a keyboard or mouse or pointer, a display, or other device that can be configured to provide input to or get output from the implantable electronics unit 102. The input provided by the external device 128 can indicate the degree of patient discomfort, such that the implantable electronics unit 102 can switch from the first electrode configuration to the second electrode configuration and provide subsequent electrostimulations. The external device 128 can include a user interface 308, which can display various options to provide the input indicating the degree of patient discomfort to the implantable electronic device 102 within the specified time period. In an example, the input or feedback can be a binary-value indicating the degree of patient discomfort. The binary-value can indicate a "yes" or "no", identifying whether there is any discomfort or not. In an example, the input indicative of the degree of patient discomfort within a specified range may have more than two values. In an example, the number of values can be equal to the number of available electrode configurations, allowing the user to rank among multiple electrode configurations in accordance with the associated discomfort. For instance, the physician can rank an electrode configuration in terms of numerals such as 1, indicating a lesser degree of discomfort or 10 indicating a greater degree of discomfort. In an example, the input can be in the form of percentage indicating the percentage of discomfort associated with the electrode configuration, such as with respect to an original degree of discomfort associated with the first electrode configuration within the specified time period. For instance, the user can provide input 25% indicating the 25% discomfort associated with the electrode configuration, or other percentage, such as 80% or 200%, for example.

In an example, the external device can present a set of suitable electrode configurations among the available electrode configurations, which set can include a specified number (e.g., 2, 3, 4, etc.) of electrode configurations, such as those that were previously deemed by the user as suitable, such as from a discomfort perspective. An electrode configuration can then be selected from the electrode configurations that were indicated by the user to be suitable. The implantable electronics unit 102 can switch from the first electrode configuration to the selected second electrode configuration. The external device 128 can display alert message or any other message sent by the implantable electronics unit 102, such as to inform the physician, patient, or any other user about the selected second electrode configuration or other information. If the controller circuit 124 determines that all the identified candidate electrode configurations have already been tested, then the implantable electronics unit 102 can return to the original (e.g., the first) electrode configuration, and can send a message to the user indicating that all the available electrode configurations were tested. If the controller circuit 124 does not receive the input confirming the degree of discomfort associated with the electrode configuration within the specified time period, then the implantable electronics unit 102 can return to the original (e.g., the first) electrode configuration, and can send an alert message to user. The external device 128 can include or can be coupled to a printer such as for printing a graphical or other representation of the information received from the implantable electronics unit 102, or the external device 128 can include a display screen such as for providing a graphical or other representation of the information.

Figure 4:
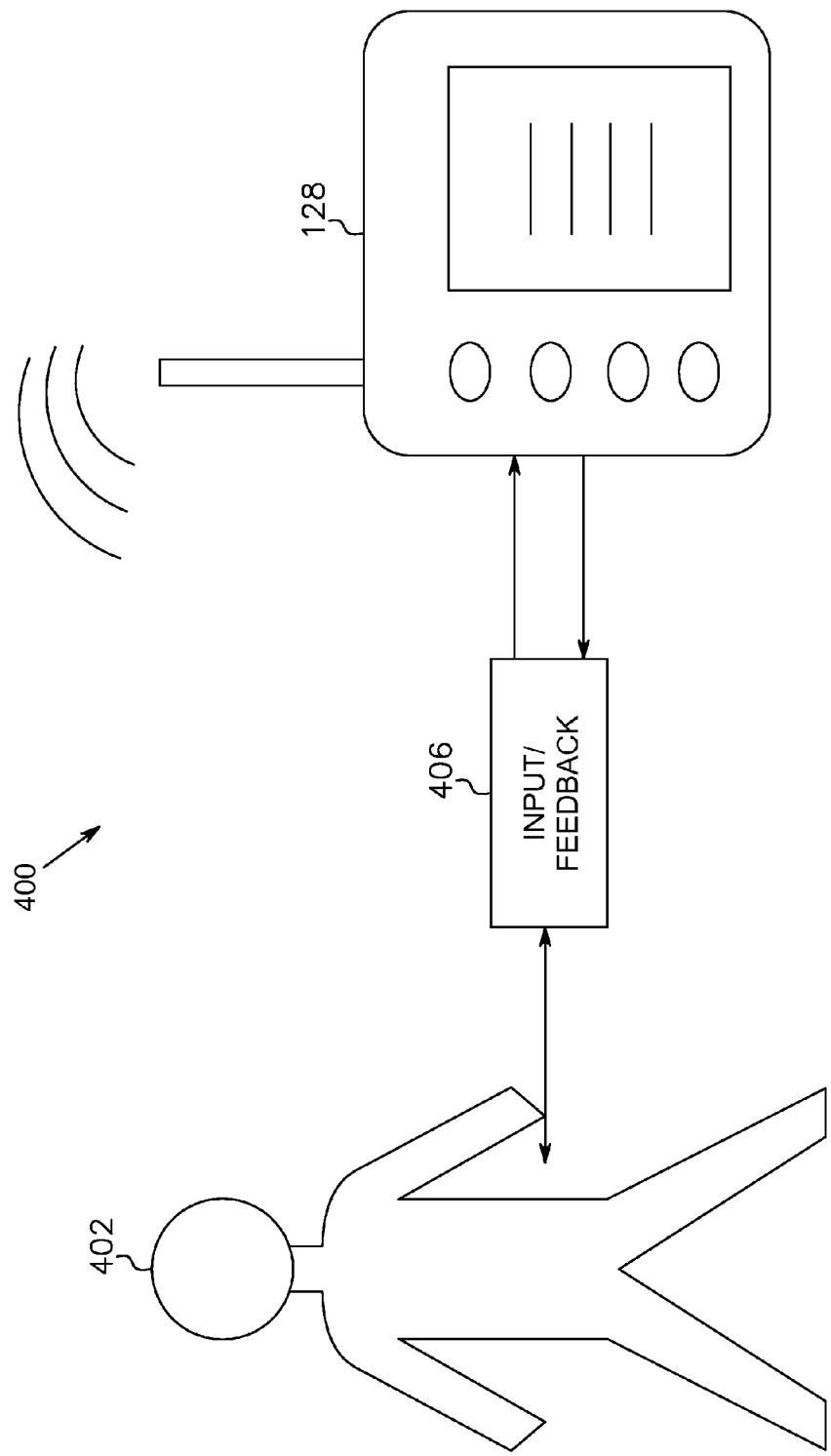
FIG. 4 illustrates an example of an external device for use in programming the implantable electronic unit of FIG. 1.

FIG. 4 illustrates an example of the external device 128, which can be configured for interfacing with or controlling the implantable electronics unit 102 of FIG. 1, or for displaying information received from the implantable electronics unit 102. The control of the implantable electronics unit 102, or the generation of a graphic display of information received from the implantable electronics unit 102 can use or be subject to user input. In an example, the patient can exercise at least some control over the electrode configuration, energy setting, or other electrostimulation configuration characteristic of the implantable electronics unit 102. Therefore, the patient may not feel the need to visit a hospital or a physician.

The control of the implantable electronics unit 102 can be by a physician or any other healthcare provider in a local clinic or from a remote location. The external device 128 can present various menus on the display screen for controlling operations of the implantable electronics unit 102 or transferring the control to a remote user.

A programming session between the implantable electronics unit 102 and the external device 128 can be initiated after receiving the input or feedback 406 through the external device 128. The input or feedback 406 can be a binary value indicating the degree of patient discomfort. In an example, the input indicative of the degree of patient discomfort within a specified range may have more than two values, such as described elsewhere herein. The input quantifying the degree of patient discomfort from the physician 402 can allow the implantable electronics unit 102 to switch from the first electrode configuration to the second electrode configuration, such as described elsewhere herein.

Figure 5:
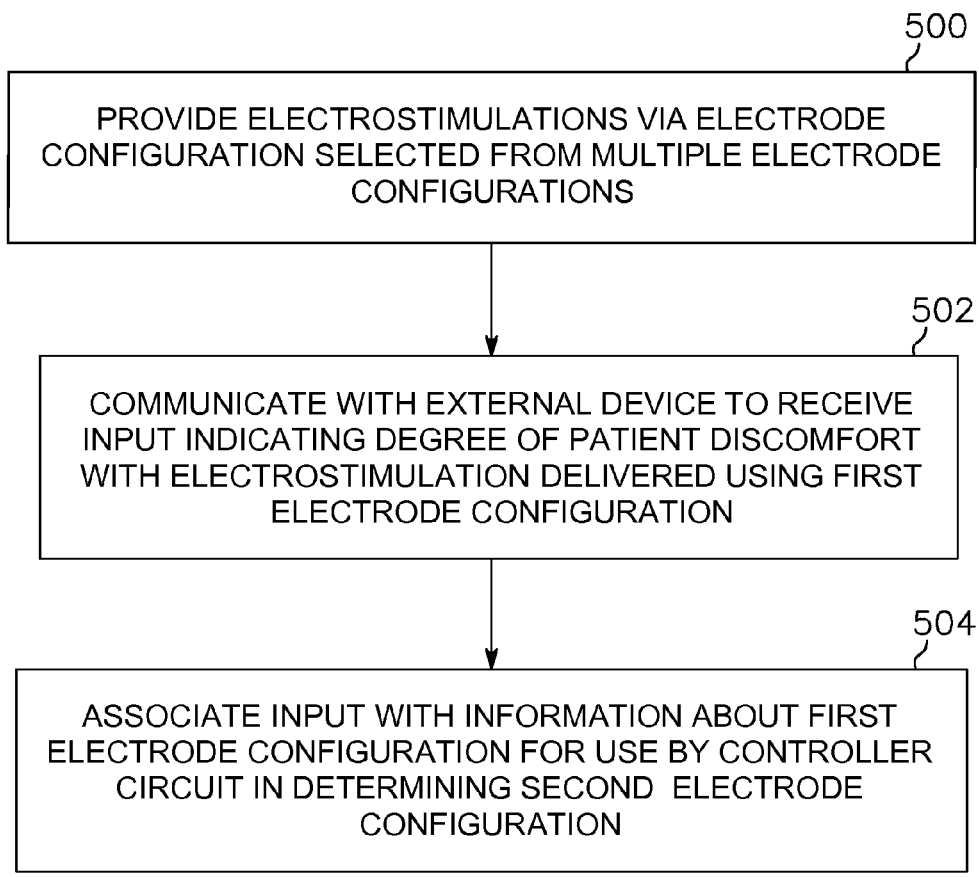
FIG. 5 is a diagram illustrating an example of a method of selecting one or more electrode configurations.

FIG. 5 is a diagram illustrating generally, by way of example, but not by way of limitation, an example of portions of a method of selecting one or more electrode configurations. Some of the illustrated acts can be performed by a physician or other users, such as externally via the external device 128. Others can be performed by the implantable electronics unit 102. The diagrams presented herein can provide the basis for a control program that can be used by a microprocessor 300 or a microcontroller or equivalent such as to effectuate the desired control of the implantable electronics unit 102 or the external device 128.

At 500, the electrostimulation circuit 122 can provide electrostimulations via an electrode configuration selected from multiple electrode configurations. The electrostimulations can be of the type for inducing a heart contraction or a neurostimulation response. When the patient senses discomfort, the patient or other user can provide an indication of one or more of the discomfort or the degree of discomfort, an indication of a need or desire for a change in electrostimulation energy associated with the first electrode configuration, or an indication of a need or desire to switch from a first electrode configuration to a second electrode configuration.

At 502, the implantable electronics unit 102 can communicate with the local or remote external device 128 such as to receive the input indicating the degree of patient discomfort with the electrostimulation delivered using the first electrode configuration.

At 504, the input (e.g., information about the degree of discomfort) can be associated with information about the corresponding first electrode configuration, such as for use by the controller circuit 124, such as for determining the second electrode configuration for delivering a subsequent electrostimulation or for changing electrostimulation energy. The second electrode configuration can be selected with the goal of substantially reducing the patient discomfort, such that the patient can be more comfortable relative to the first electrode configuration. In an example, the controller circuit 124 can search within a stored listing of various available electrode configurations, and corresponding discomfort information, to determine the second electrode configuration. The controller circuit 124 can determine whether the electrostimulation energy can be adjusted (e.g., decreased) such as to reduce the degree of patient discomfort while obtaining the desired heart contraction response or the neurostimulation response, e.g., for meeting the goal of reduced discomfort, before resorting to switching from the first electrode configuration to the second electrode configuration.

Figure 6A:
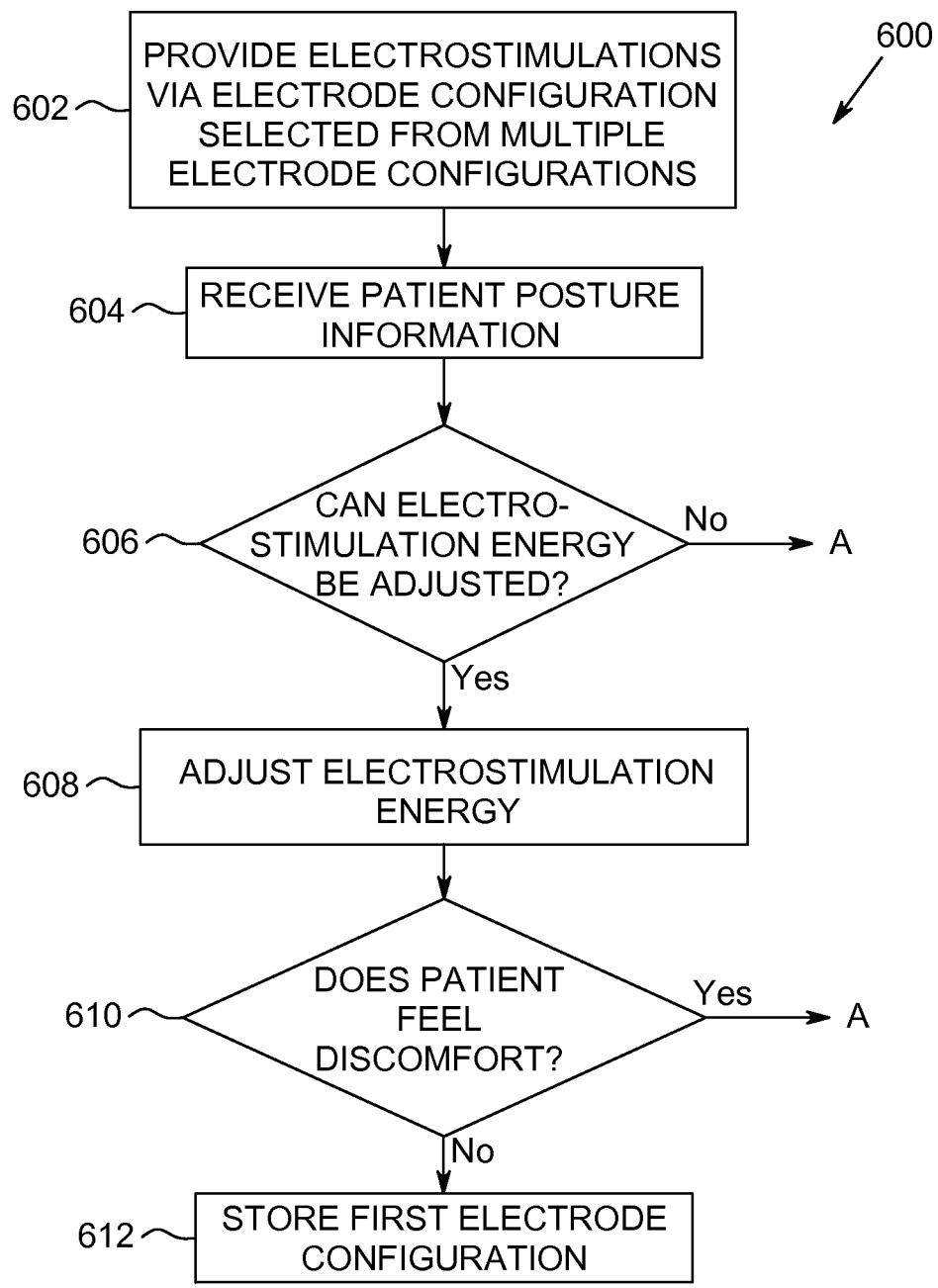
FIGS. 6A and 6B depict a diagram illustrating in detail an example of a method of selecting one or more electrode configurations.
Figure 6B:
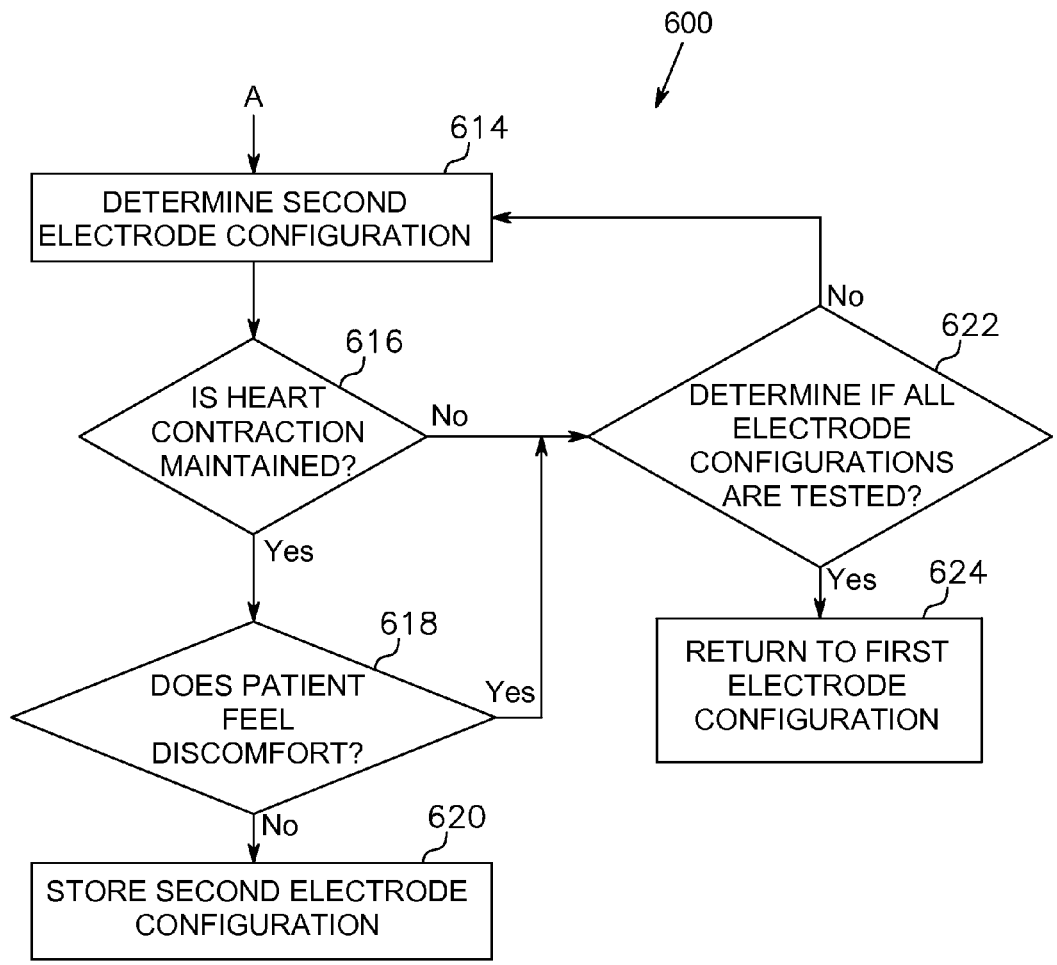

FIGS. 6A and 6B depict a diagram illustrating generally an example of portions of a method 600 of selecting one or more electrode configurations. At 602, the electrostimulation circuit 122 can provide electrostimulations of an electrostimulation energy using an electrode configuration selected from multiple electrode configurations. The electrostimulations can be of the type for inducing a heart contraction or a neurostimulation response. At 604, the controller circuit 124 can receive one or more representative signals, such as pertaining to patient posture information, extra cardiac information such as phrenic nerve stimulation or muscle stimulation, or other patient information, while maintaining the desired heart contraction or neurostimulation response of the patient. At 606, the controller circuit 124 can determine whether the electrostimulation energy can be adjusted to reduce the degree of patient discomfort while maintaining the desired heart contraction or neurostimulation response, before resorting to switching from the first electrode configuration to the second electrode configuration. If the controller circuit 124 determines that the energy can be adjusted to reduce the degree of patient discomfort while still maintaining the desired response, then at 608, the controller circuit 124 can adjust the electrostimulation energy and can use the first electrode configuration to deliver the subsequent adjusted-energy electrostimulations to the heart 106 of the patient to reduce the degree of patient discomfort. For example, the controller circuit 124 can determine whether the energy can be lowered to avoid phrenic nerve stimulation or muscle stimulation while still obtaining the desired cardiac capture or neural capture using the first electrode configuration, and, if so, can adjust the electrostimulation energy accordingly for use with the first electrode configuration to deliver the subsequent adjusted-energy electrostimulations to the heart 106.

At 610, one or more menus or options can be presented on the local or remote external device 128, such as for use by the user to indicate whether the patient still feels discomfort. At 612, if the input indicates no discomfort, then the implantable electronics unit 102 can store information representing the corresponding electrode configuration. The corresponding electrode configuration, in this case, can be the first electrode configuration. This is the initial or previously-existing electrode configuration. The electrode configuration in this instance remains unchanged because, in this example, the electrostimulation energy was adjusted while obtaining the desired response and without an unacceptable degree of discomfort to the patient. If the input indicates an unacceptable degree of discomfort, then a different electrode configuration can be determined and selected at 614, such as explained below. The input indicating the degree of discomfort can depend on that patient's tolerance level toward pain. The degree of discomfort or patient tolerance level toward pain is patient dependent; it can vary for different patients, as explained herein.

At 614, the controller circuit 124 can determine or select the second electrode configuration. This can include selecting a next electrode configuration from multiple available electrode configurations. An ordered or unordered listing or other grouping of the multiple available electrode configurations can be stored in the memory of the implantable electronics unit 102. Information identifying these multiple electrode configurations can be stored in the form of a queue. This can allow the controller circuit 124 to test the next electrode configuration identified from the queue, such as to select the second electrode configuration while maintaining the desired heart contraction or neurostimulation response. The queue can be configured by the physician or any other health care provider. The "queue" does not limit searching for the second electrode configuration in a serial manner, rather the searching can be performed in a random manner, an intelligent manner, or another manner that need not represent the sequence in which the electrode configurations information is stored in the memory.

In an example, at 616, the controller circuit 124 can determine whether the desired heart contraction or the neurostimulation response can be maintained at the second electrode configuration determined at 614. In other words, the controller can verify or test whether the desired cardiac capture or neural capture is obtained. The control circuit 124 can include an automatic electrode configuration selection module 206, which can be configured to determine or select the second electrode configuration. This can involve using the information from the extracardiac stimulation detector circuit 204, using the input indicating the degree of patient discomfort with an electrostimulation delivered using the first electrode configuration, or using both, to select the next candidate electrode configuration for use as the second electrode configuration. The controller circuit 124 can be configured to reprogram the electrostimulation circuit 122 to switch from delivering electrostimulations using the first electrode configuration to delivering electrostimulations using the determined second electrode configuration.

At 618, the patient can use one or more menus or options available on the external device 128 to provide further input, such as when the patient continues to feel discomfort. If the input indicates no unacceptable continuing discomfort, then at 620 the implantable electronics unit 102 can store identification of the second electrode configuration and electrostimulations can then be delivered using the second electrode configuration. If the input indicates a continuing unacceptable degree of discomfort, then at 622 a different electrode configuration can be determined. The controller circuit 124 can revert from the second electrode configuration to the first electrode configuration, if input confirming suitability of the second electrode configuration is not received within a specified time period. At 622, the controller circuit 124 can determine whether all identified candidate electrode configurations stored in the memory have already been tested for selecting the second electrode configuration. If not, then at 614 searching for the second electrode configuration can continue with another candidate electrode configuration. This can continue until all the identified stored candidate electrode configurations have been tested. However, if at 622 the controller circuit 124 determines that all the identified candidate electrode configurations have already been tested, then at 624, the implantable electronics unit 102 can return to the original, e.g., the first electrode configuration, or can select the electrode configuration with lowest indicated degree of discomfort. An alert message can be sent to the patient or physician indicating that all the available electrode configurations were tested. In an example, the implantable electronics unit 102 can allow the user to review allowed available electrode configurations or subset of available electrode configurations to determine whether another subset can be selected and tested. In an example, the implantable electronics unit 102 can allow the user to review more subsets of electrode configurations.

In an example, the electrostimulation circuit 122 can be reprogrammed, such as to change from delivering electrostimulations using the first electrode configuration to delivering electrostimulations using the determined second electrode configuration, in case a change is made from the first electrode configuration. The electrostimulation circuit 122 can additionally or alternatively be reprogrammed to switch from delivering electrostimulations with an adjusted electrostimulation energy in case a change is made in the electrostimulation energy.

The methods and apparatus are described with respect to implantable cardiac rhythm management (CRM) apparatus or system, such as pacemakers, cardioverter or defibrillators, pacer or defibrillators, and multi-chamber or multi-site (in a single or multiple heart chambers) cardiac resynchronization therapy (CRT) devices or devices that need not necessarily modulate heart rate. Such CRT devices can be grouped under CRM apparatus even though these devices need not necessarily (but often can) modulate heart rate. Moreover, the present methods and apparatus also find application in other implantable or external medical devices. For example, the present methods and apparatus can be included in an implantable or external neurostimulation device, such as a vagus stimulation device, a baroreceptor stimulation device, or other neurostimulation device.

In the above detailed description, reference is made to the accompanying drawings, which form a part hereof, and that is shown by way of illustrating specific examples. The examples may be combined, or that other examples may be utilized and that structural, logical, and electrical changes may be made. The above detailed description is, therefore, not to be taken in a limiting sense, and the scope of the invention is defined by the appended claims and their equivalents.

In the appended claims, the terms "including" and "in which" are used as the literal English equivalents of the respective terms "comprising" and "wherein." Also, in the following claims, the terms "including" and "comprising" are open-ended, i.e., a system, device, article, or process that includes elements in addition to those listed after such a term in a claim are deemed to fall within the scope of that claim. Moreover, in the following claims, the terms "first," and "second," etc. are used merely as labels and are not intended to impose numerical requirements on their objects.

In this document, the terms "a" or "an" are used, as common in patent documents, to include one or more than one. In this document, the term "or" is used to refer to a "non-exclusive or" unless otherwise indicated. Furthermore, all publications, patents, and patent documents referred to in this document are incorporated by reference herein in their entirety as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

What is claimed is:

1. An apparatus comprising:
    an implantable electronics unit, the implantable electronics unit including:
        an electrostimulation circuit, configured to provide a first electrostimulation to a target tissue using a first electrostimulation energy and a first electrode configuration selected from multiple electrode configurations;
        a communication circuit, configured to communicate with an external device to receive an input indicating a degree of patient discomfort produced by unintended stimulation of a non-target tissue different from the target tissue by the first electrostimulation delivered using the first electrostimulation energy and the first electrode configuration; and
        a controller circuit, coupled to the electrostimulation circuit and the communication circuit, the controller circuit comprising a stimulation detector circuit configured to detect the unintended stimulation of the non-target tissue, wherein the controller circuit is configured to use information about the degree of patient discomfort to provide a second electrostimulation using at least one of a second electrostimulation energy that is different from the first electrostimulation energy or a second electrostimulation configuration that is different from the first electrostimulation configuration.

2. The apparatus of claim 1,
    wherein the communication circuit is configured to communicate with the external device to receive the input indicating the degree of patient discomfort, quantified within a specified range, associated with the first electrostimulation delivered using the first electrode configuration;
    wherein the controller circuit is configured to associate information about the corresponding first electrostimulation energy with information about the corresponding first electrode configuration for use in determining the second electrode configuration for delivering the subsequent second electrostimulation.

3. The apparatus of claim 1,
    wherein the controller circuit is configured to first test whether the first electrostimulation energy can be adjusted to reduce the degree of patient discomfort while obtaining a desired heart contraction or a desired neurostimulation response before switching from the first electrode configuration to the determined second electrode configuration to reduce the degree of patient discomfort.

4. The apparatus of claim 1,
    wherein the controller circuit is configured to also associate information about the corresponding patient posture with information about the corresponding first electrode configuration for use in determining the second electrode configuration for delivering the subsequent electrostimulation.

5. The apparatus of claim 1,
    wherein the implantable electronics unit comprises a memory circuit configured to store information about the degree of discomfort associated with individual electrode configurations of the multiple electrode configurations.

6. The apparatus of claim 5,
    wherein the memory circuit is configured to store information about the electrostimulation energy associated with the degree of discomfort associated with the individual electrode configurations of the multiple electrode configurations.

7. The apparatus of claim 1,
    wherein the stimulation detector circuit includes an extracardiac stimulation detector circuit, and wherein the controller circuit is configured to determine the second electrode configuration at least in part using information from the extracardiac stimulation detector circuit and information from the input indicating the degree of patient discomfort with the first electrostimulation delivered using the first electrode configuration.

8. The apparatus of claim 1,
    wherein the controller circuit includes an automatic electrode configuration selection module that is configured to determine the second electrode configuration at least in part using information about at least one of a capture threshold, an electrostimulation impedance, or a posture.

9. The apparatus of claim 1,
wherein the input indicating the degree of patient discomfort provides a binary-valued indication of the degree of patient discomfort.

10. The apparatus of claim 1,
wherein the input indicating the degree of patient discomfort provides an indication quantifying the degree of patient discomfort, within a specified range having more than two values.

11. The apparatus of claim 1,
wherein the input indicating the degree of patient discomfort provides an indication quantifying the degree of patient discomfort, within a specified range having at least ten values.

12. The apparatus of claim 1,
wherein the controller circuit is configured to reprogram the electrostimulation circuit to switch from delivering the electrostimulations using the first electrode configuration to delivering the electrostimulations using the determined second electrode configuration; and
wherein the controller circuit is configured to revert from the second electrode configuration to the first electrode configuration unless an input confirming suitability of the second electrode configuration is received within a specified time period.

13. The apparatus of claim 12, wherein the controller circuit is configured to revert from the second electrode configuration to the first electrode configuration unless an input confirming suitability of the second electrode configuration in a plurality of postures is received within a specified time period.

14. The apparatus of claim 1,
wherein the stimulation detector circuit includes an extracardiac stimulation detector circuit; and
wherein the controller circuit is configured to switch between (1) determining the second electrode information using information from the input indicating the degree of patient discomfort with the electrostimulation delivered using the first electrode configuration; and (2) determining the second electrode configuration using information from the extracardiac stimulation detector circuit.

15. The apparatus of claim 14,
wherein the controller circuit is configured to use the input to switch between (1) and (2).

16. An apparatus comprising:
an implantable electronics unit, the implantable electronics unit including:
an electrostimulation circuit, configured to provide a first electrostimulation to a target tissue using a first electrostimulation energy and a first electrode configuration selected from multiple electrode configurations;
a communication circuit, configured to communicate with an external device to receive an input indicating a degree of patient discomfort produced by unintended stimulation of a non-target tissue different from the target tissue by the first electrostimulation delivered using the first electrostimulation energy and the first electrode configuration; and
a controller circuit, coupled to the electrostimulation circuit and the communication circuit, the controller circuit comprising a stimulation detector circuit configured to detect the unintended stimulation of the non-target tissue, wherein the controller circuit is configured to associate information about the degree of patient discomfort associated with the first electrostimulation with information about the corresponding first electrode configuration, for use in determining a second electrode configuration for delivering a subsequent electrostimulation.

\* \* \* \* \*